(12) United States Patent  
Voillat (10) Patent No.: US 8,021,151 B2
(45) Date of Patent: Sep. 20, 2011

(54) SURGICAL DEVICE, IN PARTICULAR A DENTAL DEVICE, COMPRISING AN INSTRUMENT AND A SERVO-CONTROL MODULE

(75) Inventor: Jean-Pierre Voillat, Montavon (CH)

(73) Assignee: Dassym SA, Neuchatel (CH)

( * ) Notice: Subject to any disclaimer, the term of this patent is extended or adjusted under 35 U.S.C. 154(b) by 1095 days.

(21) Appl. No.: 11/400,597

(22) Filed: Apr. 7, 2006

(65) Prior Publication Data

US 2006/0240382 A1    Oct. 26, 2006

Related U.S. Application Data

(63) Continuation of application No. PCT/EP2004/052497, filed on Oct. 11, 2004.

(30) Foreign Application Priority Data

Oct. 10, 2003  (CH) ...................................... 1734/03

(51) Int. Cl.
*A61C 1/02*    (2006.01)
(52) U.S. Cl. ........................................................ 433/99
(58) Field of Classification Search ............... 433/98, 433/99, 101, 102, 103, 114, 118, 131, 133; 606/60–78
See application file for complete search history.

(56) References Cited

U.S. PATENT DOCUMENTS

| | | | | |
|---|---|---|---|---|
| 4,305,126 A | * | 12/1981 | Beier et al. ...................... | 433/28 |
| 5,689,159 A | * | 11/1997 | Culp et al. ............... | 318/400.18 |
| 2002/0182564 A1 | * | 12/2002 | Katsuda et al. .................. | 433/98 |
| 2004/0059197 A1 | * | 3/2004 | Yamashita et al. ............ | 600/300 |
| 2004/0231473 A1 | * | 11/2004 | Geibler et al. .................. | 82/124 |
| 2009/0094398 A1 | * | 4/2009 | Eng .............................. | 710/305 |

FOREIGN PATENT DOCUMENTS

| | | |
|---|---|---|
| EP | 0 254 215 A1 | 1/1988 |
| EP | 0 688 539 A1 | 12/1995 |
| WO | WO 98/14129 | 4/1998 |

* cited by examiner

*Primary Examiner* — Cris L Rodriguez
*Assistant Examiner* — Sunil K Singh
(74) *Attorney, Agent, or Firm* — Pearne & Gordon LLP (57) ABSTRACT

A surgical device includes a manual instrument provided with a rotary motor for driving a tool and at least one sensor for determining at least one operating parameter of the motor (1). The device further includes an electronic servo-control module of the motor, and a flexible connection for electrically connecting the instrument to the electronic module. The instrument includes a digital electronic circuit for processing output signals of the sensor and transmitting them to the electronic module through the flexible connection.

46 Claims, 9 Drawing Sheets

SURGICAL DEVICE, IN PARTICULAR A DENTAL DEVICE, COMPRISING AN INSTRUMENT AND A SERVO-CONTROL MODULE

REFERENCE DATA

The present invention is a continuation of international application PCT/EP2004-052497 (publication WO05037124), filed on Oct. 11, 2004, the content of which is enclosed by reference. PCT/EP2004-052497 claims priority of Swiss Patent Application CH2003-01734 of Oct. 10, 2003, the content of which is enclosed by reference.

FIELD OF THE INVENTION

The present invention concerns a surgical device, in particular a dental device, comprising an instrument, for example a manual instrument, provided with a rotary motor for driving a tool and an electronic servo-control module of this motor.

BACKGROUND OF THE INVENTION

Such devices are frequently used for example in the field of dentistry. The device comprises, or is constituted of, a hand part that can be provided for example with a bur, another rotating tool, or a device driven by a rotary motor. The electronic servo-control module is often connected to the patient's chair and connected to the manual instrument by a flexible connection containing electric leads and passage tubes for air and water.

The rotary motors used in this type of hand part are more and more often motors without collectors and without brushes, which have the advantage of being more robust and being capable of being sterilized completely. In order to avoid excessive heating of the instrument, which can be called upon to turn at considerable speeds, for example up to 40'000 turns per minute, three-phase motor are preferable.

Such dental devices are described for example in documents EP688539, U.S. Pat. No. 5,543,695, EP1228737, EP1302173, WO0105023, WO01/45248, EP1109301 or WO0004631, to which the reader will refer advantageously.

It is important for the user of this type of device to control the instrument's rotation speed accurately and over a large range. A torque control is also necessary for example to stop the rotation before the tool breaks. In the prior art, solutions are therefore known in which the manual instruments are provided with sensors making it possible to detect at any time the angular position or the rotor speed of the motor. The motor is servo-controlled with set-point values determined taking into account the measurement signals supplied by these sensors.

In order to increase the flexibility of the connection between the servo-control module and the instrument, it is necessary to limit the number of electric leads going through this connection. The connections that are commercially available and accepted by the users thus comprise two, or at most four electric leads.

In the case of a three-phase motor, three of these leads are used for powering stator coils (phases of the motor). The fourth lead is often used for controlling the lamp or another accessory associated with the hand part. No electric conductor is thus available for transmitting the measurement signals supplied by the sensor to the electronic servo-control module.

Different solutions exist in the prior art in which the servo-controlling electronics are completely loaded in the manual instrument. This type of hand part is however voluminous, heavy and thus difficult to handle. Furthermore, the cost of a set of several instruments that all include servo-control electronics becomes prohibitive.

Other solutions have been suggested in which the servo-control module injects on at least one of the phase conductors a high-frequency signal deformed by the stator and rotor magnetic fields. The measuring of this deformation on the return conductors allows the rotor's angular position to be determined. This method is however not very robust and does not allow reliable and accurate measurements to be performed.

Other servo-control solutions used employ non-standard connections with more than four electric leads.

Other solutions further require the rotor's configuration to be modified, for example its shape or the arrangement of the magnets, to allow a measurement without loaded electronics. These solutions do not apply with standard commercial motors and set important additional constraints during manufacture of the motor.

One aim of the present invention is thus to propose an improved instrument allowing the mentioned problems of the prior art to be resolved.

One aim of the present invention is in particular to propose an improved device in which the rotor's angular position can be determined with an accuracy and a resolution on the order of 1 degree, and this on a very large speed range, for example from 1 to 40'000 turns per minute.

Another aim is to increase the possibilities for control, measure and servo-control of an instrument of this type.

BRIEF DESCRIPTION OF THE INVENTION

According to the invention, these aims are achieved by means of a device having the characteristics of claim 1.

In particular, these aims are achieved by means of a surgical device, in particular a dental device, having:

an instrument provided with a rotary motor for driving a tool and at least one sensor for determining at least one motor operating parameter, an electronic servo-control module of this motor, a flexible connection for connecting electrically the instrument with the electronic module, wherein the instrument includes a digital electronic circuit for processing the output signals of the sensor and for transmitting them to the electronic module through the flexible connection.

The digital processing of the measurement data supplied by the sensor or sensors allows the amount of information needing to be transmitted to the servo-control module to be reduced considerably. For example, instead of supplying to the electronic module crude analog output signals of the sensor or sensors, the digital electronic circuit can supply at periodical intervals digital words indicating the rotor's angular position. These words can be transmitted for example in series by means of a digital modulation method on one of the motor's phase conductors or on the available fourth lead.

In the other way, the digital electronic circuit and the instrument can be controlled by the electronic module by means of digital control messages. It is thus possible to control very flexibly the operation of the sensor or sensors, of the motor, of the digital electronic circuit and of possible auxiliary circuits.

Optimal flexibility of measurement and control can thus be achieved thanks to this bidirectional digital dialog between the electronic servo-control module and the instrument. The digital processing of the measurement data also allows the measurement errors caused by electrostatic or electromagnetic perturbations during transmission to be reduced.

The digital electronic circuit in the instrument can also process and transmit information supplied by other sensors or devices of the instrument or connected to the instrument, for example torque sensors, temperature sensors, switches, duration of bulb use detectors, type of tool detectors, etc.

DESCRIPTION OF THE DRAWINGS

The present invention will be better understood by reading the description of a preferred embodiment illustrated by the figures, in which.

DETAILED DESCRIPTION OF THE INVENTION

The inventive surgical device is preferably a manual instrument and includes for example a motor in its casing as well as a hand part bearing a tool driven by the motor. Such a device is for example partly illustrated in FIG. 18. The device includes an instrument 100 whose motor 1 is represented. The motor 1 preferably has a nose or hooking 11 designed to receive for example a hand part, not represented. The instrument 100 thus comprises the motor 1 and for example the hand part. The invention however also applies to devices wherein the motor, the hand part and possibly even the tool form a single piece.

Figure 18:
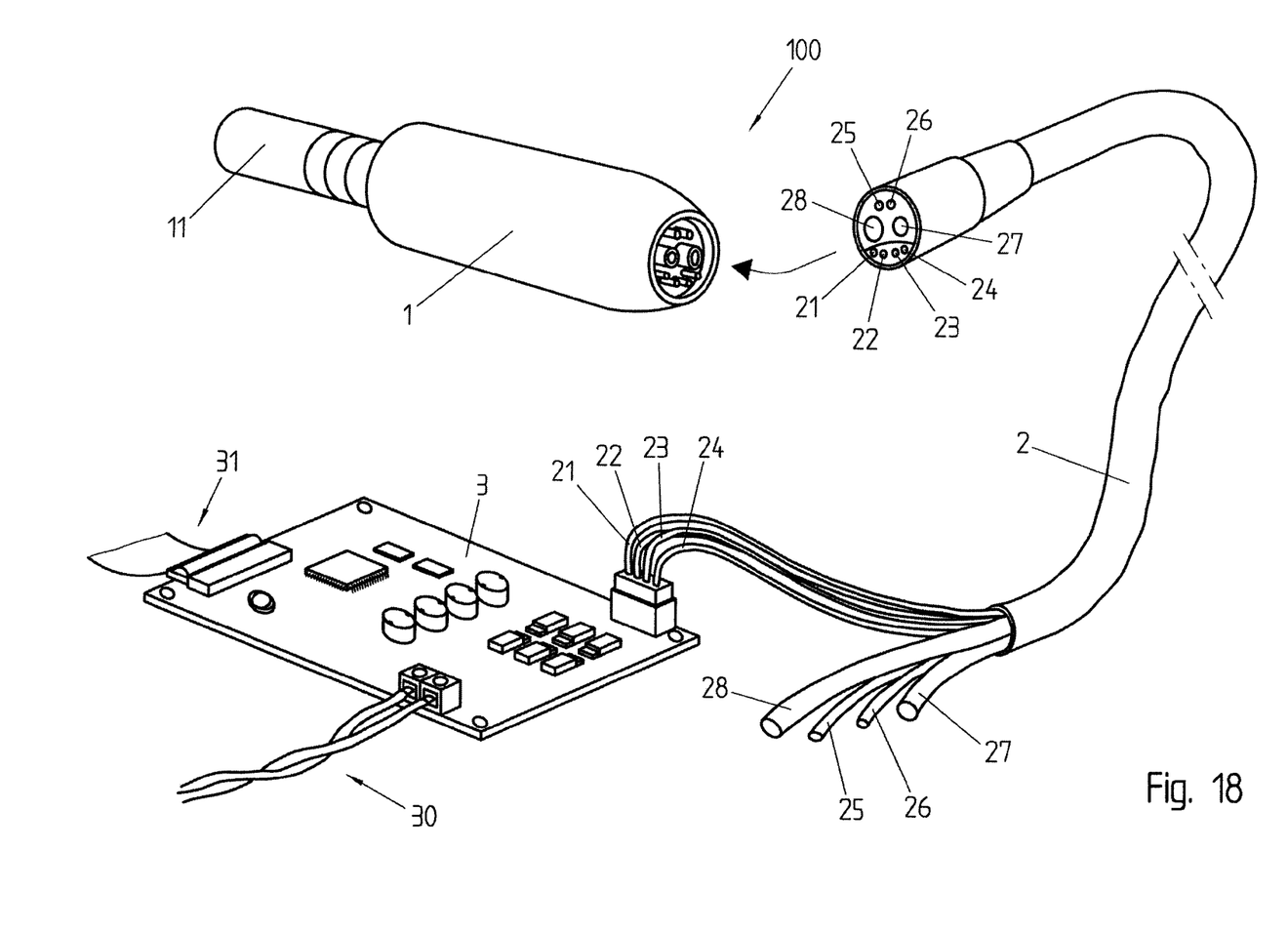
FIG. 18 shows a surgical device according to a preferred embodiment of the invention.

The instrument 100 is preferably connected to a servo-control module 3 through a flexible connection, for example a flexible tube 2 attached to the motor 1. The instrument 100 is fed for example with water, with air and with electricity through the tube 2. In the case of a dental device, the tube 2 includes for example four electric contacts 21, 22, 23, 24 and tubes 25, 26, 27, 28 for the passage of air and/or of liquid. The air and/or liquid passage tubes preferably have a water feed conduit 25 for a spray, an air feed conduit 26 also for the spray, a cold air feed conduit 27 designed for cooling the motor 1 and an air return conduit 28.

The tube 2 is connected at its other extremity to one or several air and water sources, not represented, as well as preferably to the electro servo-control module 3 designed in particular for controlling the electric powering of the motor 1. The electric contacts 21, 22, 23, 24 of the tube 2 are thus preferably connected to the electronic servo-control module 3. In the case of a three-phase motor, three of the four electric leads are for example used for electrically powering three stator windings of the motor 1, and the fourth electric lead 24 is for example connected electrically to an electric accessory of the instrument 100 or of the hand part of the instrument, for example to a lamp allowing the instrument's work zone to be lit.

The electronic servo-control module 3 is furthermore connected, for example by means of an electric cable 30, to an electric power source, not represented, for example a continuous voltage source supplying for example a 34 volt voltage. The electronic servo-control module 3 is preferably also connected to a control bus 31 through which it can for example communicate with a numerical command, not represented, a control panel, etc.

Acquisition of the Position of the Motor

The Elements of the Acquisition

According to one embodiment of the invention, the instrument includes means for acquiring the angular position of the rotor of the motor 1.

Figure 1:
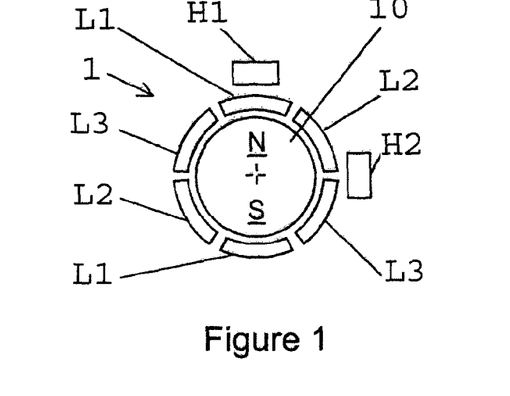
FIG. 1 represents a brushless motor with a rotor and three windings.

FIG. 1 illustrates diagrammatically the motor 1 of is an instrument according to a preferred embodiment of the invention. The motor 1 is for example a brushless motor including a rotor 10 and three windings L1, L2, L3. It can thus be a three-phased collectorless motor having three stator windings L1, L3, L3 mounted in a star. The motor 1 further comprises two sensors H1, H2 allowing at least one motor operating parameter to be determined. The sensors H1, H2 are for example analog sensors with Hall effect or magneto-resistive ones making it possible to determine the instantaneous angular position α of the rotor 10. They are arranged for example between the rotor 10 and the stator L1, L2, L3 or outside the stator 10. The two sensors H1, H2 are preferably arranged so as to form together an angle of 90°.

Figure 19:
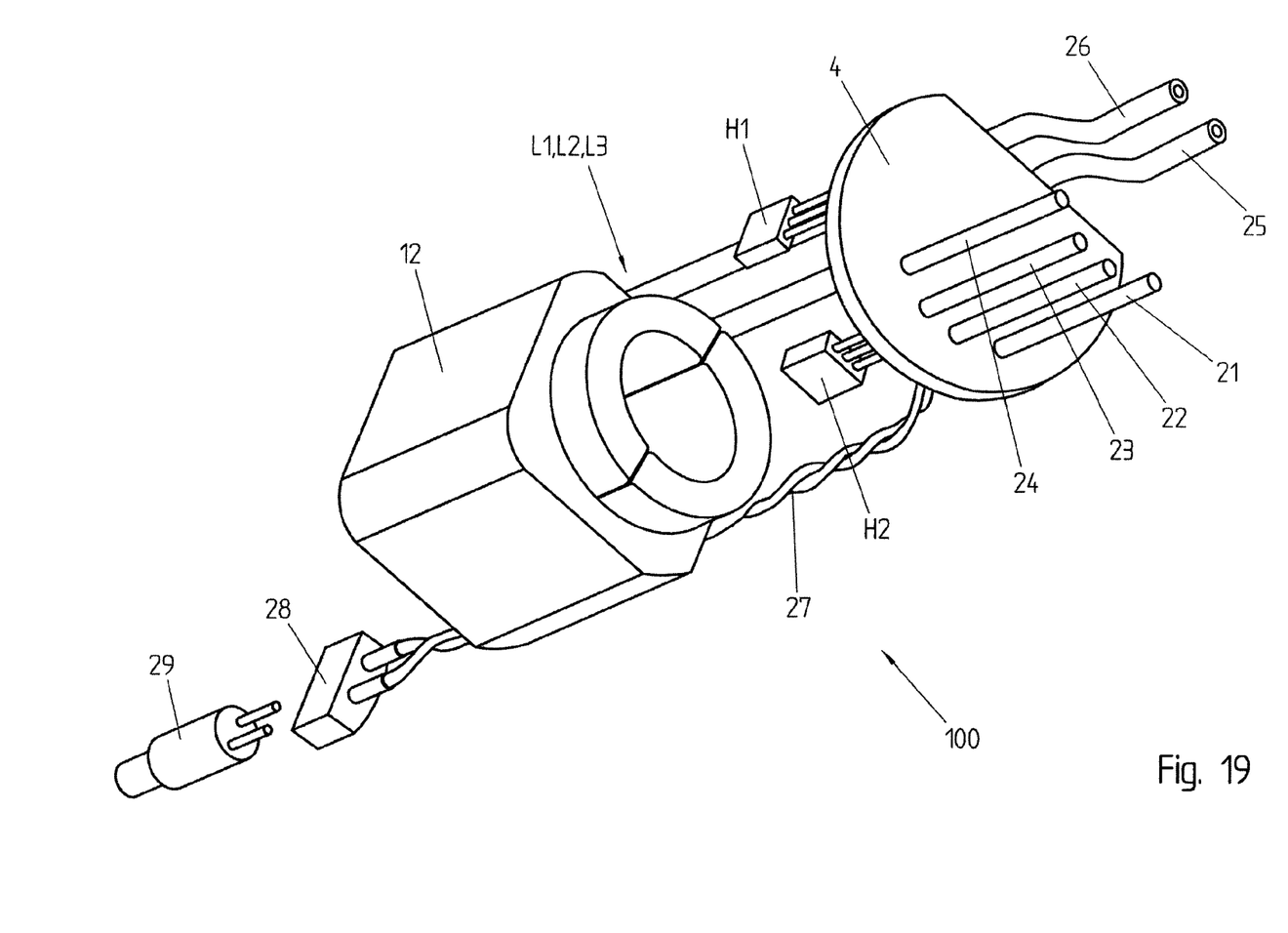
FIG. 19 is an exploded view of some inside elements of the motor of the device of FIG. 18.

FIG. 19 is an exploded view of some inside elements of the instrument 100 of the surgical device according to a preferred embodiment of the invention. Barring any contrary indication, the same reference signs designate the same elements in all the figures.

According to a preferred embodiment of the invention, the instrument 100 includes a loaded digital electronic circuit 4 that preferably has a microcontroller, not represented. The reference 12 designates the motor's stator yoke. A shield, not represented, is preferably provided between the stator windings L1, L2, L3 of the motor 1 and the digital electronic circuit 4.

The electric contacts 21, 22, 23, 24 preferably stand in direct contact with the digital electronic circuit 4 to which are also connected the sensors H1, H2. The digital electronic circuit 4 is preferably mounted on a printed circuit board perpendicular to the motor's rotation axis. The sensors H1, h2 are then for example mounted directly onto the printed circuit board.

When the instrument 100 is mounted, the sensors H1, H2 are for example lodged in a recess in the stator sheets of the motor 1 and/or in a recess between the rotor 10 and the stator.

The instrument 100 further includes for example an electric accessory. The electric accessory is preferably a bulb 29, for example a LED, allowing the work zone to be lit. The bulb 29 is for example held in a socket 28 powered by an electric feed cable 27. One of the terminals of the electric accessory is for example connected to one of the leads 24 dedicated to this use, to one of the motor's phase conductors 21, 22, 23 and/or to the neutral point between the motor phases. One of the terminals of the electric accessory can also be connected to the digital electronic circuit 4. The operation of the electric accessory is then for example controlled by the digital electronic circuit 4.

Figure 2:
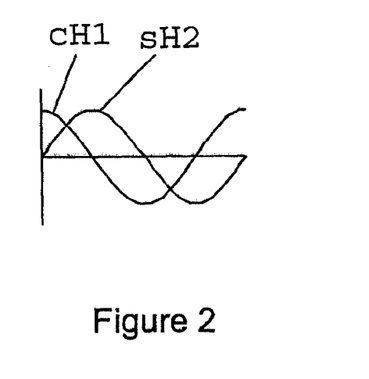
FIG. 2 represents electric signals in cosine and sine generated by the movement of the motor's rotor of FIG. 1.

The rotation of the rotor 10 generates respectively on the sensors H1 and h2 a cosine electric signal cH1 and a sine electric signal sH2, represented in FIG. 2. Preferably, the signals cH1 and sH2 are proportional respectively to the cosine and to the sine of the angle $\alpha$ or angular position $\alpha$ of the rotor 1.

It is possible to extract the tangent of the angle $\alpha$ or angular position $\alpha$ of the rotor 1 by performing:

$tg(\alpha) = sH2/cH1$.

Extracting the Tangent of the Position Angle

Unfortunately, the tangent tends towards infinity. In order to avoid this disadvantage, any extraction of the is tangent is preferably carried into the zone 0°-45° and then replaced in its original zone.

According to a preferred embodiment of the invention, an extraction rule is established according to the conditions set out in the following table:

| | | | | |
|---|---|---|---|---|
| 0°-45° | cH1 ≧ 0 | sH2 ≧ 0 | \|cH1\| ≧ \|sH2\| | $tg\alpha_0 = tg(0°) + tg[\|sH2\| / \|cH1\|]$ $\alpha = 0° + \alpha_0$ |
| 45°-90° | | | \|sH2\| ≧ \|cH1\| | $tg\alpha_1 = tg(45°) - tg[\|cH1\| / \|sH2\|]$ $\alpha = 90° - \alpha_1$ |
| 90°-135° | cH1 < 0 | | \|sH2\| ≧ \|cH1\| | $tg\alpha_2 = tg(0°) + tg[\|cH1\| / \|sH2\|]$ $\alpha = 90° + \alpha_2$ |
| 135°-180° | | | \|cH1\| ≧ \|sH2\| | $tg\alpha_3 = tg(45°) - tg[\|sH2\| / \|cH1\|]$ $\alpha = 180° - \alpha_3$ |
| 180°-225° | | sH2 < 0 | \|cH1\| ≧ \|sH2\| | $tg\alpha_4 = tg(0°) + tg[\|sH2\| / \|cH1\|]$ $\alpha = 180° + \alpha_4$ |
| 225°-270° | | | \|sH2\| ≧ \|cH1\| | $tg\alpha_5 = tg(45°) - tg[\|cH1\| / \|sH2\|]$ $\alpha = 270° - \alpha_5$ |
| 270°-315° | cH1 ≧ 0 | | \|sH2\| ≧ \|cH1\| | $tg\alpha_6 = tg(0°) + tg[\|cH1\| / \|sH2\|]$ $\alpha = 270° + \alpha_6$ |
| 315°-0° | | | \|cH1\| ≧ \|sH2\| | $tg\alpha_7 = tg(45°) - tg[\|sH2\| / \|cH1\|]$ $\alpha = 360° - \alpha_7$ |

The first column of the table determines zones for the value of the angular position $\alpha$. The second, third and fourth columns indicate the conditions fulfilled by the cosine signals cH1 and sine signals sH2 as well as by their absolute values \|cH1\| resp. \|sH2\| in each of these zones. The fifth column of the table indicates the formula making it possible for each zone to calculate the tangent of the angular position $\alpha_n$ (n=0-7) of the rotor carried into the angular zone 0°-45°. The rotor's angular position $\alpha$ is then computed for each zone according to the formula expressed in the table's last column.

Figure 3:
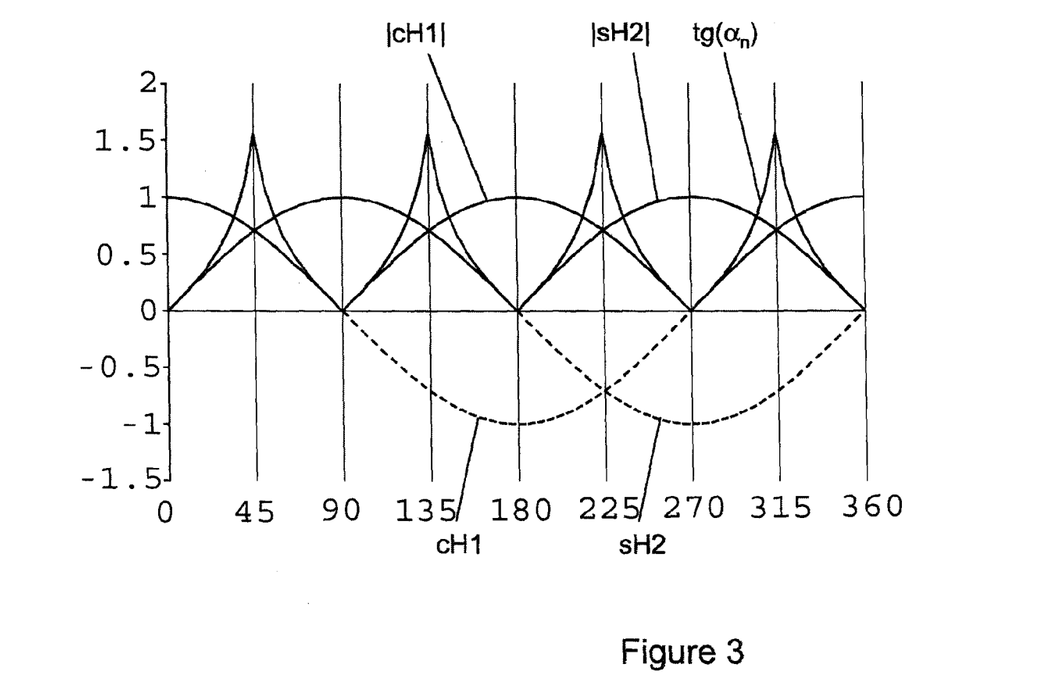
FIG. 3 illustrates the extraction of the tangents of the angular position of the motor of FIG. 1.

FIG. 3 shows the extraction of the tangents $\alpha_n$ (n=0-7). It illustrates in particular the cosine signals cH1 and sine signals sH2, the absolute values \|cH1\| resp. \|sH2\| of these signals as well as the tangent $tg(\alpha_n)$ of the angular position $\alpha_n$ (n=0-7) of the rotor carried into the angular zone 0°-45°.

Determining the Angular Position

Figure 4:
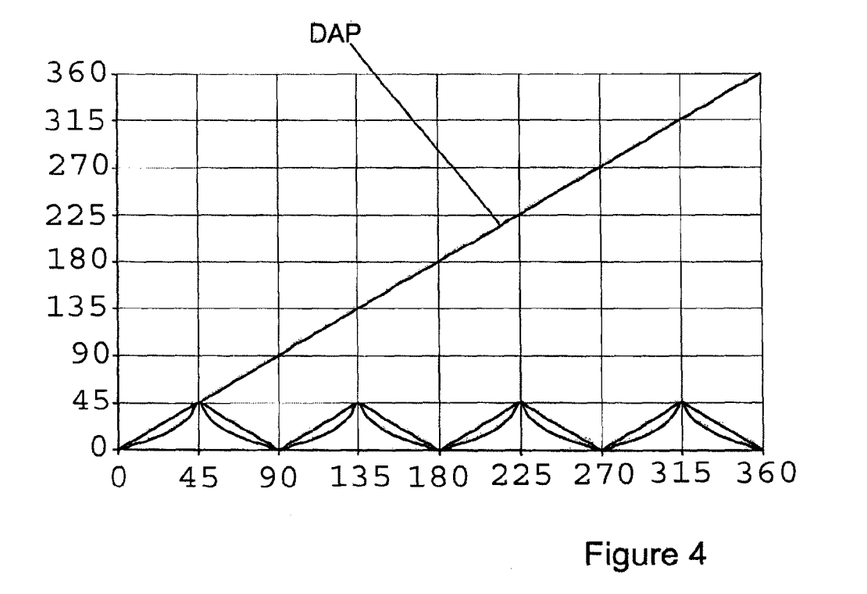
FIG. 4 illustrates the position acquisition line (DAP)

FIG. 4 illustrates the determining of the angular position of the rotor of the motor of the inventive device. The figure shows the angle $\alpha_n$ (n=1, ..., 7) whose computation of the tangent is indicated in the above table and whose value varies between 0° and 45°. The angular position $\alpha$ of the motor's rotor is represented by the position acquisition line DAP. It is computed from the value of $\alpha_n$ according to the formula given for each angular zone in the table's last column.

Figure 5:
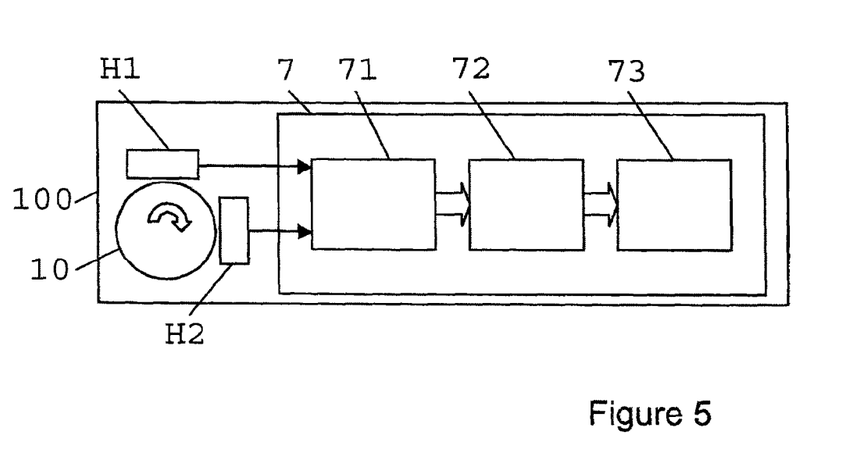
FIG. 5 represents diagrammatically the device for acquiring the angular position of the rotor of the motor of FIG. 1 according to an embodiment of the invention.

The acquisition of the angular position $\alpha$ of the rotor 10 of the motor 1 is preferably directly computed according to the method explained here above by the instrument's loaded digital electronic circuit. The digital electronic circuit loaded in the instrument 100 preferably includes a loaded microcontroller 7 performing the acquisition of the angular position $\alpha$ of the rotor 10 of the motor 1 according to the principle illustrated in FIG. 5. The analog signals generated by the sensors H1, H2 when the rotor 10 of the instrument's motor 1 rotates are sent to the microcontroller 7 that converts them into digital signals by an analog/digital conversion module 71. The analog/digital conversion 71 is followed by a mathematical processing step by a module 72 during which the digital data are processed according to the method described further above. The mathematical processing step by the module 72 is followed by a step of determining the digital value by a module 73 during which the result of the mathematical processing by the module 72 will be used to determine, with the aid of the position acquisition DAP line illustrated in FIG. 3 a digital value corresponding to the angular position of the rotor 10.

Loaded Electronics

Figure 6:
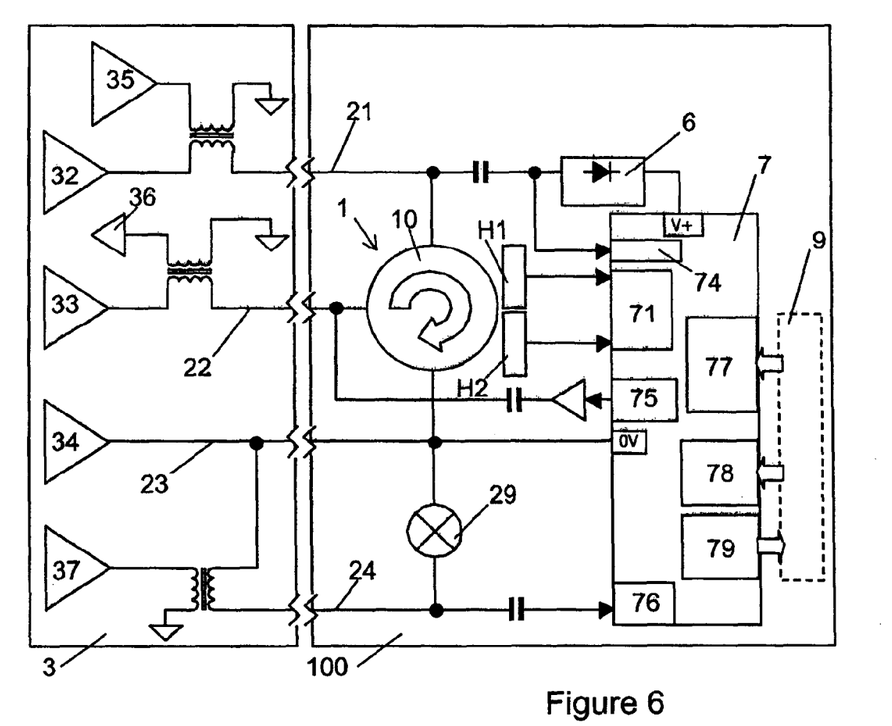
FIG. 6 shows a synoptic diagram of the electronics loaded in the instrument according to one embodiment of the invention.

FIG. 6 gives the synoptic diagram of the electronics according to a preferred embodiment of the invention. Part of the electronics represented diagrammatically is situated on the electronic servo-control module 3 that serves in particular to feed and control the instrument 100 whilst another part of the electronics is loaded in the instrument 100. The distribution of the electronic elements between the electronic servo-control module 3 and the instrument 100 can however be modified within the frame of the invention.

The elements designated by certain reference numbers in FIG. 6 are described hereafter:

32: Analog power driver of the phase I of the motor 1.
33: Analog power driver of the phase II of the motor 1.
34: Analog power driver of the phase III of the motor 1.
35: Amplifier inserting high frequency on phase 1, e.g. 2 Mhz, supplying the powering and the synchronism of the loaded microcontroller 7.
36: Amplifier receiving the information emitted by the microcontroller 7 loaded in the instrument.
37: Power driver for the lamp 29 and FSK modulator for emitting data towards the loaded microcontroller 7.
7: Loaded microcontroller including preferably the following functions and/or elements:
  Synchronizer 74: to ensure unperturbed information transmissions, it is important that they should be synchronized with the high frequency (for example at 2 Mhz) powering of the loaded microcontroller 7.
  Output data 75: according to a preferred embodiment of the invention, the information emitted by the loaded microcontroller 7 work at half of the high frequency according to a principle described further below. The information emitted by the loaded microcontroller 7 thus work for example at 1 Mbaud, i.e. half of 2 Mhz.

Input data 76: the lamp 29 is fed by a voltage AC of 350 kHz. The data transfer from the electronic module 3 to the microcontroller 7 occurs through frequency modulation according to the frequency-shift-keying (FSK) technique, for example at a frequency of 350 kHz±25 kHz.

Auxiliary inputs/outputs 78 resp. 79: the microcontroller 7 is able to transmit, besides the DAP line, auxiliary information (analog or digital) coming from control or measure elements, also loaded.

29: Lamp.

9: Optional auxiliary functions, for example control and measure elements, or active elements triggered by the electronic servo-control module 3, etc.

Figure 7A:
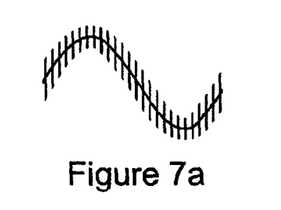
FIGS. 7a, 7b, 7c and 7d represent the electric signals transmitted between the electronic servo-control module and the motor according to one embodiment of the invention.

21: Phase I conductor of the motor 1 on which the motor's driving component (low-frequency signal) and the high-frequency loaded feed component of the microcontroller 7 are transmitted (FIG. 7a).

Figure 7B:
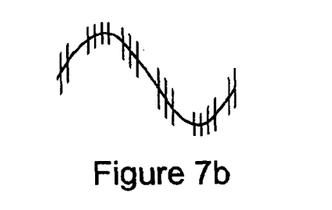

22: Phase II conductor of the motor 1, on which the motor's driving component and the component for example at 1 Mbaud of the data transmitted from the microcontroller 7 to the module 3 are transmitted (FIG. 7b).

Figure 7C:
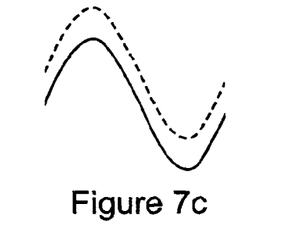
Figure 7D:
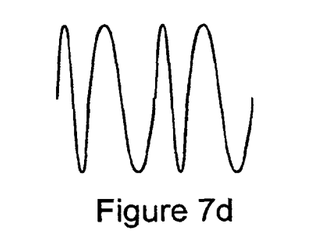

23: Phase III conductor of the motor 1. This phase is the neutral conductor from the high frequency point of view. The "0V" (gnd) of the microcontroller 7 follows the motor's driving component represented by the lower curve of FIG. 7c. The upper component is the exact replica of the lower component with an additional 5V and connected to "V+" of the microcontroller 7 of the instrument 100. "V+" is generated by the rectified high frequency of phase I without its low frequency component.

24: Conductor for feeding the lamp 29 and conveying the information transmitted from the module 3 to the microcontroller 7. The lamp 29 is fed with a current-regulated AC voltage of a frequency of about 350 kHz. The information destined to the microcontroller 7 loaded in the instrument 100 are encoded by frequency modulation (±25 kHz).

6: Rectifier allowing for example the digital electronic circuit loaded in the instrument 100 to be fed electrically. The rectifier 6 rectifies for example a high-frequency signal injected by the module 3 into one of the electric conductors, for example on the conductor 21. The loaded digital electronic circuit, in particular the microcontroller 7, is then fed electrically by the output of the filter of the rectifier 6.

Information from the Microcontroller to the Module

Between the microcontroller 7 and the electronic servo-control module 3, the transmission is of the serial type. The data are thus transmitted serially according to the principle illustrated in FIG. 8. The signal 81 is the feed high frequency, for example at 2 MHz, transmitted on the motor's phase I. The signal 82 represents the information flux, for example at 1 Mbaud, transmitted on the phase II.

Figures 8, 9:
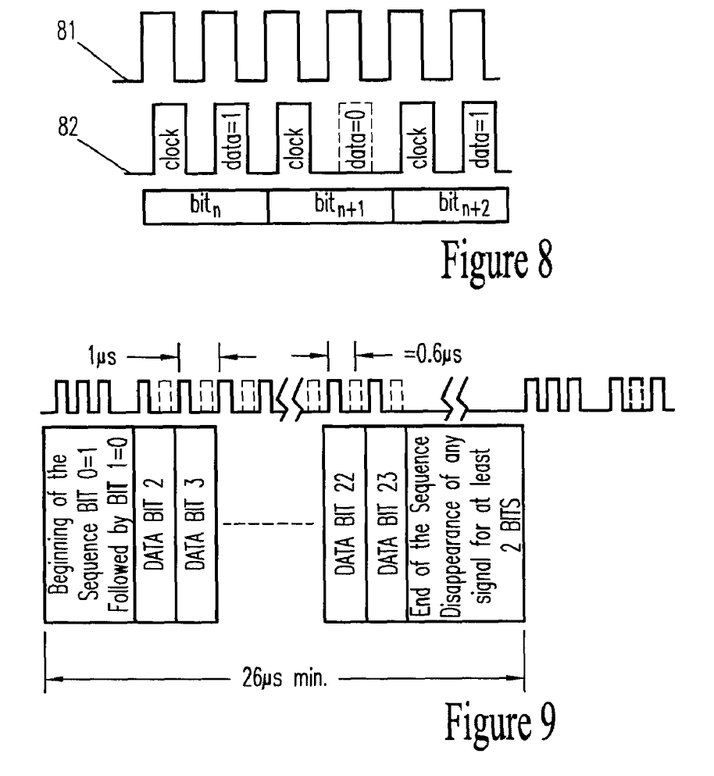
FIG. 8 represents a clock signal and a corresponding combined clock/data signal according to one embodiment of the invention.
FIG. 9 represents a message according to one embodiment of the invention.

It arises from FIG. 8 that whatever the bit value, it is always preceded by the clock pulse. The minuteness of the loaded electronics does not allow the microcontroller to be "clocked" by a quartz but by a RC circuit of relative stability.

Level 1 Protocol (Hardware Level)

With reference to FIG. 9, a word is composed for example of 24 bits, including two bits BIT0, BIT1 of the SEQUENCE START and 22 data bits DATABIT2, . . . , DATABIT 23. The end of the word is for example signaled by the absence of signal during at least 2 bits, which represents for example an END SEQUENCE of an interval of 2 µs.

Other word lengths, sequence starts and/or end sequences are however perfectly conceivable in the frame of the invention.

Level 2 Protocol (Bit Allocation)

Figure 10:
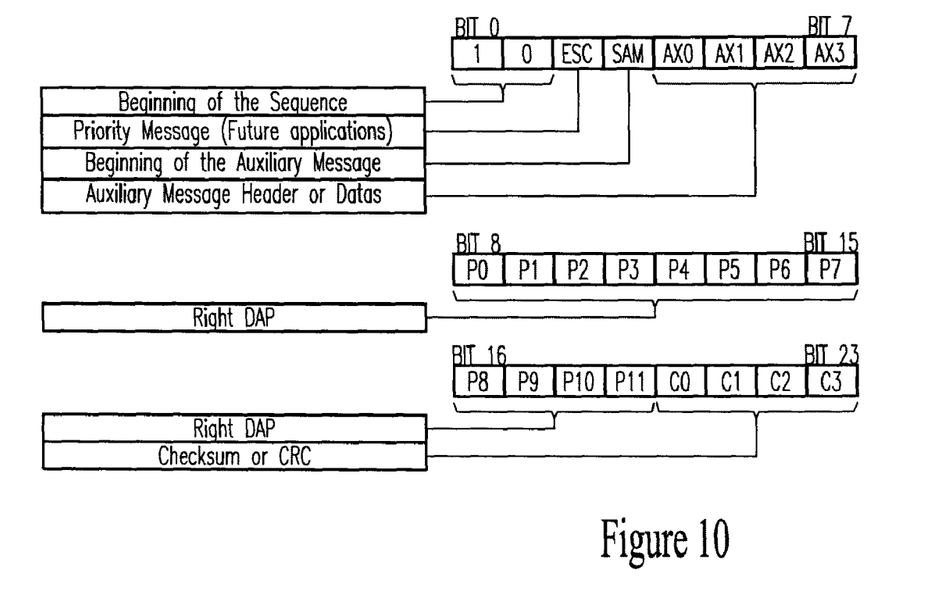
FIG. 10 illustrates the allocation of the bits of the sent messages by the microcontroller according to one embodiment of the invention.

The bit allocation of the messages sent by the loaded microcontroller 7 to the electronic module 3 is preferably defined as illustrated in FIG. 10. Other allocation modes are however perfectly conceivable within the frame of the invention. The number of bits allocated to each function and/or the number and the type of functions can in particular be modified according to need.

Auxiliary Messages

Auxiliary messages mean any information not pertaining to the rotor's angular position. This information is generated in the instrument by the auxiliary functions 9 of FIG. 7.

Figure 11:
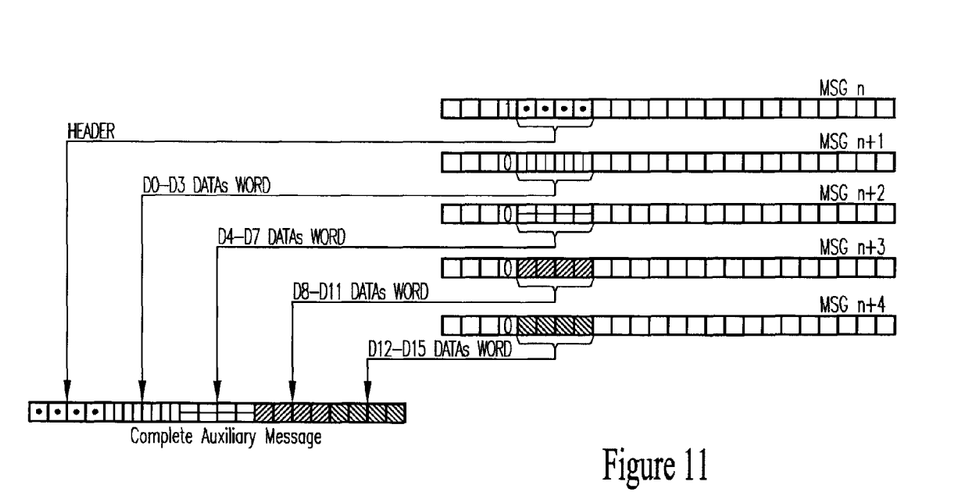
FIG. 11 illustrates the structure of an auxiliary message according to one embodiment of the invention.

Each auxiliary message is for example composed of a HEADER, for example of 4 bits, and of a DATA WORD, for example of 16 bits, transmitted according to a preferred embodiment as shown by FIG. 11. Other forms of transmitting and/or encoding auxiliary messages are however conceivable in the frame of the invention.

Information from the Module to the Microcontroller

According to a preferred embodiment of the invention, the communication from the electronic servo-control module 3 to the microcontroller 7 is performed by frequency modulation on the lamp conductor 24.

The transmission of information from the electronic servo-control module 3 to the microcontroller 7 can however also be performed on another conductor 21, 22, 23 and with the aid of other modulation methods.

Servo-Controlling the Motor

Driving the Motor's Instrument

Figure 12A:
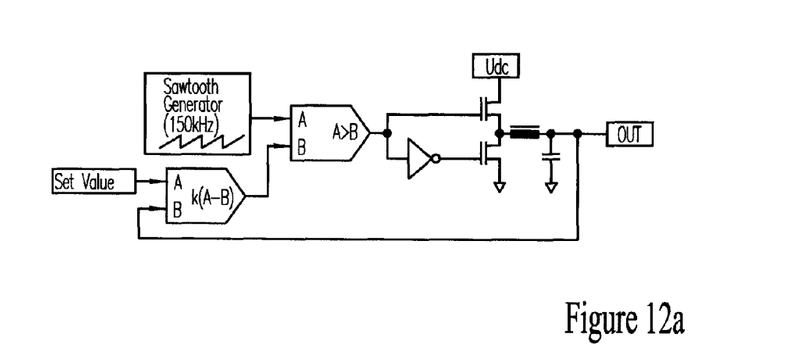
FIG. 12a is a functional diagram of the drivers according to one embodiment of the invention.
Figure 12B:
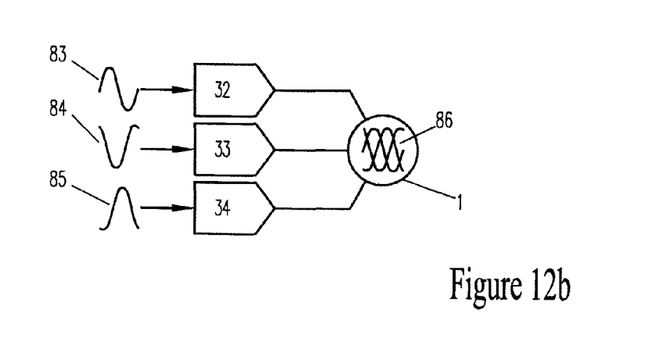
FIG. 12b illustrates a three-phased motor controlled by three drivers.

According to the preferred embodiment of the invention, the motor 1 is driven by three analog drivers 32, 33, 34 supplying sinusoidal signals 83, 84, 85 forming a field rotated 86 phase-shifted by 120° of variable amplitude and frequency (FIG. 12b). The choice of such a driving provides two considerable advantages:

Better engine power of the motor 1 over the whole speed range.

Very "soft" rotation, essentially at low speeds.

In one embodiment, the system works with "all or nothing" drivers.

The basic principle of the drivers according to an embodiment of the invention is illustrated diagrammatically in FIG. 12a. Other types of drivers are however conceivable in the frame of the invention.

Servo-Controlling the Position

Basic Principle for Setting in Rotation

Figure 13:
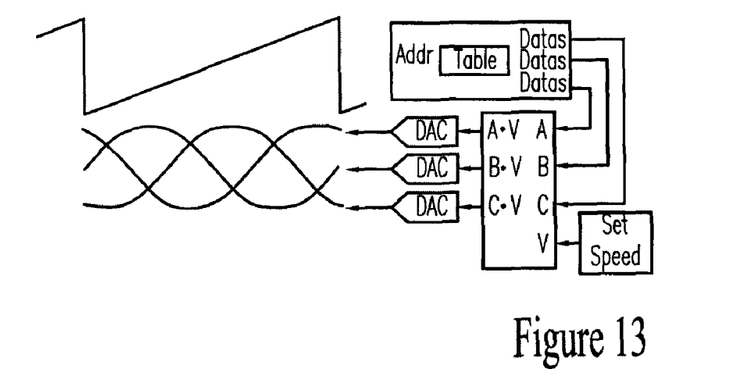
FIG. 13 illustrates diagrammatically a basic principle for making the motor rotate.

In its basic principle, setting the motor in rotation according to a preferred embodiment of the invention is simple. It is enough to create a table that, from the addressing given by the digital value of the DAP line, will supply three sinus values phase-shifted by 120°. The motor's speed is then defined by the amplitude common to the three sinuses, as represented diagrammatically in FIG. 13.

Compensation of the Geometric Position of the Hall sensors

Figure 14:
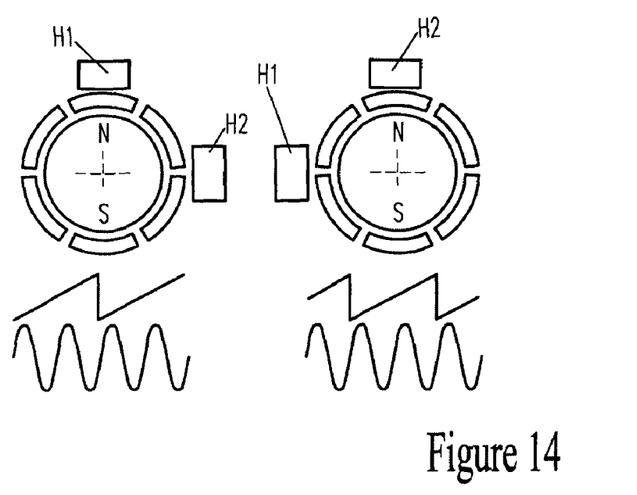
FIG. 14 shows different geometric positions of the Hall sensors.
Figure 15:
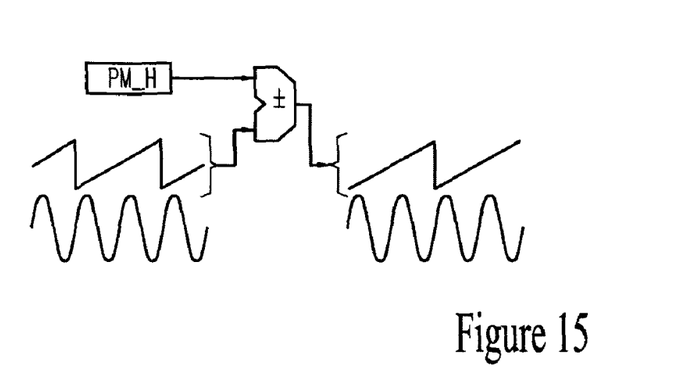
FIG. 15 illustrates a compensation process of the geometric position of the Hall sensors.

The relation between the phase of the analog control signals and the phase of the DAP line depends on the position of the Hall sensors H1, H2, as illustrated in FIG. 14 that shows two possible arrangements. To compensate this effect, it is preferably necessary to add a signed parameter (±PM_H) on the DAP line, taking into account the modulo[360°]. FIG. 15 illustrates the compensation circuit according to an embodiment of the invention.

Compensation of the Re-Actualization Angle $\alpha_R$

The acquisition of the angular position $\alpha$ of the rotor 10 and the resulting computations take a certain time, typically about 50 µs, during which the motor turns. This means that the re-actualization of the drivers 32, 33, 34 of the motor 1 depends on a reading of the angular position $\alpha$ that is outdated. This difference in position or re-actualization angle $\alpha_R$ is insofar greater as the speed of the motor 1 is great; in fact, it is directly proportional to the motor's speed.

Figure 16:
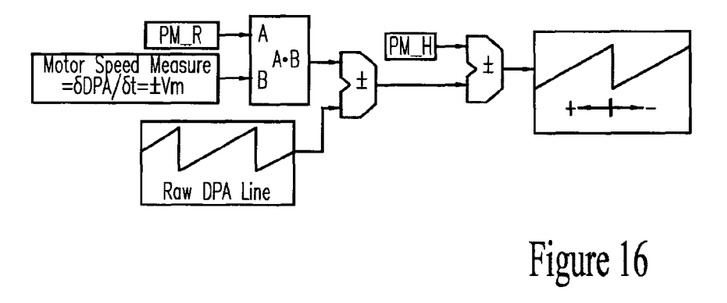
FIG. 16 illustrates a compensation device of the re-actualization angle.

A preferred embodiment for compensating this difference consists in adding to the DAP line modulo[360°] a value proportional to the signed speed ($\pm V_M$). The proportionality constant is defined by the parameter PM_R. FIG. 16 shows the compensation device according to an embodiment of the invention.

Compensation of the Pursuit Angle $\alpha_P$

The pursuit angle $\alpha_P$ is the angle formed by the magnetic vector of the field rotated 86 and that of the rotor 10. This angle increases proportionally to the speed and to the torque. It is calculated by effecting:

$$\alpha_P = \text{set-point value} - DAP \text{ position}$$

Figure 17:
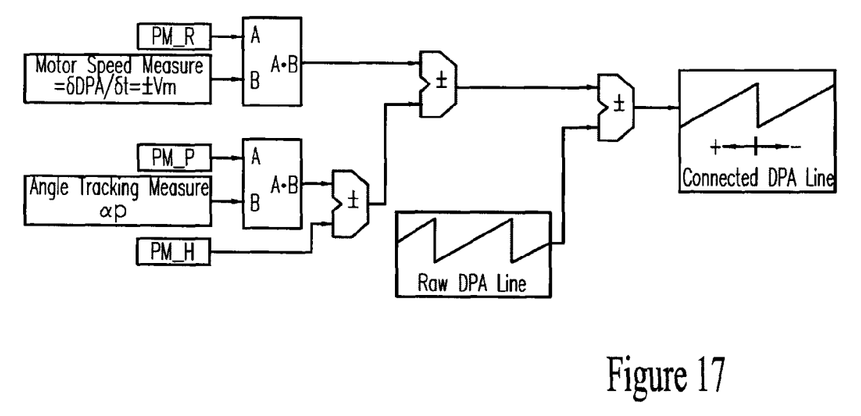
FIG. 17 shows all the compensation devices according to a preferred embodiment of the invention.

The proportionality constant is defined by the parameter PM_P and FIG. 17 shows the whole of the compensation circuits according to a preferred embodiment of the invention. It is however conceivable, within the frame of the invention, to implement only certain of the compensation circuits described here above, to implement them with the aid of different circuits or by software. Other compensation circuits not described here are further conceivable within the frame of the invention.

The invention is described here above in the frame of a dental device having four electric conductors between the servo-control module 3 and the instrument 100. The invention however also applies to other surgical devices having for example a different number of electric contacts between the servo-control module 3 and the instrument 100 on which the data and/or the feed of the loaded electronics can be transmitted.

As explained at least partially further above and with reference to FIGS. 1 to 19, the surgical device, notably the dental device, of the invention thus includes in certain variant embodiments of the invention, one or several of the characteristics recited hereafter.

The instrument 100 comprises a loaded digital electronic circuit 4 having at least one analog-digital converter, for example in the form of a module 71, for converting the analog output signals from the sensor or sensors H1, H2 into digital signals processed and transmitted to the electronic servo-control module 3. The digital electronic circuit 4 includes for example a processor 7 with the analog-digital conversion module 71. The processor 7 makes it possible more generally to process and transmit to the electronic servo-control module 3 data obtained from the output signals cH1, sH2 under control of a program. The electronic circuit 4 computes for example the tangent of the cosine signals cH1 and sine signals sH2 supplied by the two sensors H1, H2. The digital circuit preferably computes the tangent carried into a zone from 0 to 45°, with one or several bits indicating for example the used zone.

The electronic circuit 4 thus computes and transmits for example to the electronic servo-control module 3 the instantaneous angular position $\alpha$ of the rotor 10 of the motor 1. The electronic circuit 4 is for example arranged to transmit periodically, at regular intervals, to the module 3 digital data depending on the output signals cH1, sH2, with the digital data being preferably modulated digitally on one or several of the electric leads 21, 22, 23, 24 of the tube 2. The digital data are for example transmitted serially in the form of words on exactly one of the electric leads, for example on one of the phase conductors feeding the electric motor 1, the frequency used for transmitting the words being greater than the feed frequency of the motor 1. According to one embodiment, the digital words include auxiliary indications supplied by sensors or switches 9 other than the angular position is sensors H1, H2. The auxiliary indications include for example one or several of the following indications:

indications supplied by a temperature sensor in the instrument 100, indications relative to the type of tool connected to the instrument, the type of tool being for example determined automatically, indications relative to the duration of use of a bulb 29 in the instrument, indications relative to the actuating of a trigger, switch or regulating device on said instrument, indications relative to the circulation of a liquid and/or of air through the flexible connection 2, etc.

The instrument 100 includes for example a switch with two or several positions supplying a digital control signal interpreted by the digital electronic circuit 4.

The digital electronic circuit 4 preferably supplies several times per rotation of the rotor 10 to the module 3 digital data indicating the absolute angular position $\alpha$ of the rotor 10.

The electronic servo-control module 3 is preferably arranged to transmit to the digital electronic circuit 4 digital control data modulated digitally on the electric leads 21, 22, 23, 24 of the flexible connection 2. The digital control data are for example transmitted serially in the form of words on exactly one of the electric leads.

The electronic servo-control module 3 preferably comprises three power drivers 32, 33, 34 for powering the three phases of the motor 1. The three power drivers 32, 33, 34 are for example analog drivers supplying three analog signals phase-shifted by 120° and of variable frequency.

Preferably, the electronic servo-control module 3 controls the rotation speed of the motor 1. It controls for example the torque of the motor 1. Preferably, the electronic module 3 servo-controls however both the rotation speed and the torque of the motor 1, in four quadrants.

The servo-control module 3 preferably further performs a correction of the set-point value to take into account the positioning errors of the Hall sensors H1, H2 determined during the device's calibration. It preferably also performs a correction of the set-point value to take into account the rotation of the rotor 10 during the measure and the computation and/or a correction of the set-point value to compensate the pursuit angle between the stator field rotated and the field of the rotor 10. The correction performed to compensate the pursuit angle is preferably proportional to the voltage applied on the coils.

The servo-control module 3 includes for example a processor controlled by a program to control the functioning of the instrument 100. The program allows for example the machining cycle to be defined with the instrument 100, the machining cycles including for example is several to-and-fro movements with the instrument 100 or the tool for breaking chips. According to one embodiment, the program makes it possible to control the machining depth with the tool.

The instrument 100 comprises for example a CCD sensor supplying data processed by the digital circuit 4 and transmitted to the electronic servo-control module 3.

The invention claimed is:

1. A surgical device, notably a dental device, comprising:
an instrument provided with a rotary motor for driving a tool and at least one sensor for determining at least one operating parameter of said motor,
an electronic servo-control module of the motor,
an electric accessory comprising a lamp that illuminates a work zone of the instrument,
a flexible connection for electrically connecting said instrument to said electronic module, said flexible connection comprising three electric leads for electrically powering said motor and one electric lead for powering said electric accessory,
said instrument comprising a digital electronic circuit for processing the output signals of said at least one sensor and transmitting them to said electronic module through the flexible connection as digital data,
wherein said digital data is transmitted over the electric lead for powering said electric accessory by digital modulation,
wherein a terminal of said electric accessory is connected to said lead of the flexible connection used for powering said electric accessory while another terminal of said electric accessory is connected to a neutral point between phases of said motor,
wherein an operation of said electric accessory is controlled by said digital electronic circuit.

2. The device of claim 1, wherein said motor is a collectorless motor.

3. The device of claim 2, wherein said motor is a three-phased motor having three stator windings mounted in a star.

4. The device of claim 1, wherein said rotary motor has a rotor and wherein said at least one sensor allows the instantaneous angular position of said rotor to be determined.

5. The device of claim 4, wherein two Hall sensors or magneto-resistive sensors phase-shifted by 90° supply two signals in quadrature whose phase depends on the angular position of said rotor.

6. The device of claim 1, wherein said flexible connection comprises exactly four electric leads for electrically connecting said electronic servo-control module to said instrument.

7. The device of claim 6, wherein three of said four electric leads are used for electrically feeding three stator windings of said motor and wherein the fourth electric lead is connected electrically to the electric.

8. The device of claim 1, wherein said flexible connection includes tubes for the passage of air and/or liquid.

9. The device of claim 1, wherein said digital electronic circuit comprises at least one analog-digital converter for converting the analog output signals of said at least one sensor into digital signals processed and transmitted to said electronic servo-control module.

10. The device of claim 9, wherein said digital electronic circuit comprises a processor for processing and transmitting to said electronic servo-control module data obtained from said output signals under control of a program.

11. The device of claim 1, wherein said electronic circuit computes and transmits to said electronic servo-control module the instantaneous angular position of the rotor of said motor.

12. The device of claim 1, wherein said electronic circuit is arranged to transmit said digital data periodically, at regular intervals, to said module.

13. The device of claim 12, wherein said digital data are transmitted serially in the form of words on exactly one of said electric leads.

14. The device of claim 13, wherein said digital words include auxiliary indications supplied by sensors or switches other than the angular position sensors.

15. The device of claim 14, wherein said auxiliary indications include indications supplied by a temperature sensor in said instrument.

16. The device of claim 14, wherein said auxiliary indications include indications relative to the type of tool connected to said instrument, said type of tool being determined automatically.

17. The device of claim 14, wherein said auxiliary indications include indications relative to the duration of use of a bulb in said instrument.

18. The device of claim 14, wherein said auxiliary indications include indications relative to the actuating of a trigger, switch or regulating device on said instrument.

19. The device of claim 14, wherein said auxiliary indications include indications relative to the circulation of liquid and/or air through said flexible connection.

20. The device of claim 1, wherein said digital electronic circuit supplies several times per rotation of the rotor to said module digital data indicating the absolute angular position of said rotor.

21. The device of claim 1, wherein said instrument includes a rectifier for rectifying a high frequency signal injected by said module on one of the electric leads of said connection, said digital electronic circuit being fed electrically by the output of said rectifier filter.

22. The device of claim 1, wherein said electronic servo-control module is arranged for transmitting, to said digital electronic circuit, digital control data modulated digitally on the electric leads of said flexible connection.

23. The device of claim 22, wherein said digital control data are transmitted serially in the form of words on exactly one of said electric leads.

24. The device of claim 1, wherein one of the terminals of the electric accessory is connected to said digital electronic circuit.

25. The device of claim 1, wherein said electronic servo-control module includes three power drivers for feeding the three phases of said motor.

26. The device of claim 25, wherein said three power drivers are analog drivers supplying three analog signals phase-shifted by 120° and of variable frequency.

27. The device of claim 1, wherein said electronic servo-control module controls the rotation speed of said motor.

28. The device of claim 1, wherein said electronic servo-control module controls the torque of said motor.

29. The device of claim 28, wherein said electronic module servo-controls both the rotation speed and the torque of said motor.

30. The device of claim 1, wherein said servo-control module performs a correction of the set-point value to take into account the positioning errors of the Hall sensors determined during calibration of the device.

31. The device of claim 1, wherein said servo-control module performs a correction of the set-point value to take into account the rotor's rotation during measurement and computation.

32. The device of one of claim 1, wherein said servo-control module performs a correction of the set-point value to compensate the pursuit angle between the stator field rotated and the field of the rotor.

33. The device of claim 32, wherein the correction performed for compensating said pursuit angle is proportional to the voltage applied on said windings.

34. The device of claim 1, wherein said servo-control module includes a processor controlled by a program for controlling the operation of said instrument.

35. The device of claim 34, wherein said program allows to control the depth of machining with said tool.

36. The device of claim 1, wherein a shield is provided between the stator windings of said motor and said digital electronic circuit.

37. The device of claim 1, wherein said at least one sensor is lodged in a recess in the stator sheets of said motor.

38. The device of claim 1, wherein said at least one sensor is lodged in a recess between the rotor and the stator.

39. The device of claim 1, wherein said digital electronic circuit is mounted on a printed circuit board perpendicular to the rotation axis of said motor.

40. The device of claim 39, wherein said at least one sensor is mounted onto said printed circuit board.

41. The device of claim 1, wherein said instrument includes a CCD sensor supplying data processed by said digital circuit and transmitted to said electronic servo-control module.

42. A surgical instrument provided with:
a rotary motor for driving a surgical tool, said rotary motor having a rotor,
at least one sensor for determining the instantaneous angular position of said rotor,
an electric accessory comprising a lamp that illuminates a work zone of the instrument,
a digital electronic circuit for computing digital data representative of said instantaneous angular position and for transmitting said digital data over an electric lead for powering the electric accessory by digital modulation,
wherein a terminal of said electric accessory is connected to said lead for powering said electric accessory while another terminal of said electric accessory is connected to a neutral point between phases of said motor,
wherein an operation of said electric accessory is controlled by said digital electronic circuit.

43. A surgical instrument provided with:
a three-phased rotary motor for driving a surgical tool, said rotary motor having a rotor and a stator, said stator having windings,
at least one sensor for determining the instantaneous angular position of said rotor,
an electric accessory comprising a lamp that illuminates a work zone of the instrument,
three electric leads for electrically feeding said stator windings and one electric lead for electrically feeding said electric accessory,
wherein digital data representative of said instantaneous angular position is modulated onto the electric lead for electrically feeding said electric accessory,
wherein a terminal of said electric accessory is connected to the electric lead for electrically feeding said electric accessory while another terminal of said electric accessory is connected to a neutral point between phases of said motor.

44. The instrument of claim 43, wherein said digital data includes auxiliary indications supplied by sensors or switches other than the angular position sensors.

45. A surgical device, notably a dental device, comprising:
an instrument provided with a three-phased rotary motor for driving a tool and at least one sensor for determining at least one operating parameter of said motor,
an electronic servo-control module of the motor,
an electric accessory comprising a lamp that illuminates a work zone of the instrument,
a flexible connection for electrically connecting said instrument to said electronic module,
said instrument comprising a circuit for processing the output signals of said at least one sensor and transmitting them to said electronic module through the flexible connection over an electric lead for powering the electric accessory,
wherein said servo-control module performs a correction to compensate the pursuit angle between the stator field rotated and the field of the rotor, said correction being proportional to the voltage applied on said windings,
wherein a terminal of said electric accessory is connected to said lead for powering the electric accessory while another terminal of said electric accessory is connected to a neutral point between the phases of said motor,
wherein an operation of said electric accessory is controlled by said digital electronic circuit.

46. A surgical device, notably a dental device, comprising:
an instrument provided with a three-phased rotary motor for driving a tool and at least one sensor for determining at least one operating parameter of said motor,
an electronic servo-control module of the motor,
a flexible connection for electrically connecting said instrument to said electronic module, said flexible connection comprises electric leads for electrically powering said motor, said motor being powered by an AC power source in the servo-control module,
said instrument comprising a digital electronic circuit for processing the output signals of said at least one sensor and transmitting them to said electronic module through the flexible connection as digital data,
wherein said digital data is transmitted over at least one of said electric leads by digital modulation,
wherein the servo-control module inserts a high-frequency periodic signal onto one of the leads for electrically powering said motor, the high-frequency periodic signal having a higher frequency than a frequency of an AC voltage for electrically powering said motor,
wherein the digital electronic circuit receives the high-frequency periodic signal and synchronizes data transmissions from the digital electronic circuit with the high-frequency periodic signal, and wherein the instrument includes a rectifier that rectifies the high-frequency periodic signal and the digital electronic circuit is powered by an output of the rectifier.

* * * * *